US00PP10128P

United States Patent [19]

Fincham

[11] Patent Number: Plant 10,128

[45] Date of Patent: Nov. 25, 1997

[54] *PARTHENOCISSUS QUINQUEFOLIA* PLANT VARIETY NAMED 'MONHAM'

[75] Inventor: Robert Fincham, Boring, Oreg.

[73] Assignee: Monrovia Nursery Company, Azusa, Calif.

[21] Appl. No.: 644,293

[22] Filed: May 10, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—Christie, Parker & Hale, LLP

[57] ABSTRACT

A new *Parthenocissus quinquefolia* vine having variegated leaves of green marked with irregular random patterns of white in the Summer season which turn pink in the Fall season.

3 Drawing Sheets

BACKGROUND OF THE INVENTION

The present invention relates to a new and distinct variety of *Parthenocissus quinquefolia* discovered as a sport in a controlled planting of *Parthenocissus quinquefolia* in Tamaqua, Pa. The varietal denomination of the new variety is 'Monham'.

*Parthenocissus quinquefolia* is also known as "Virginia Creeper" and "Woodbine". It is characterized by ultimate, compound palmate, 3 to 5 leaves, each stalked (elliptic to obovate-oblong), about 1.5 to 4 inches long and about 0.5 to 2.5 inches wide. The leaves are acuminate, usually cuneate, coarsely and often crenately serrate, lustrous dark green above, and glaucescent beneath. Young foliage exhibits a bright waxy bronze to red coloration and a petiole of about 1 to 4 inches long.

Plants of *Parthenocissus quinquefolia* may grow 30 to 50 feet, and more, depending on the structure upon which it climbs. Its range of hardiness is generally from Zone 3 to Zone 9. Plants have a deciduous vine habit with tendrils that have about 5 to 8 branches, each ending in adhesive-like tips such that the plant has an ability to cling itself to walls or other supporting structure and, therefore, needs no additional support. It will also crawl along ground, as suggested by its common reference appellation "Virginia Creeper".

The plant grows fast, about 6 to 10 feet or more in a single season. It is valuable as a landscape plant because of its low maintenance character and ability to "climb" on supporting surfaces, e.g. walls, trees, other plants, etc.

SUMMARY OF THE INVENTION

The new variety of *Parthenocissus quinquefolia* 'Monham' possesses characteristics similar to its parent but may be distinguished by a combination of traits including leaves smaller than its parent, slower growing than its parent, and distinctively different leaf coloration. 'Monham' Summer season foliage is green marked with irregular and random patterns of white, and contains small patches (splatters) in several shades of green. In the Fall season, the green portions turn red and the white parts turn pink.

Asexual reproduction by vegetative cuttings of the new variety as performed in Oregon shows that the foregoing and other distinguishing characteristics come true to form and are established and transmitted through succeeding propagations.

BRIEF DESCRIPTION OF THE ILLUSTRATIONS

The accompanying illustrations show typical specimens of the vegetative growth of the new variety in the Summer and in the Fall.

A third illustration is included for comparison and shows vegetative growth of the parent variety with its uniformly green foliage.

The Summer season foliage exhibits green leaf coloration marked with irregular, random patterns of white and small patches (splatters) in varying shades of green.

One illustration shows Fall turning coloration illustrating that the white parts turn pink which may be contrasted with the Summer season foliage.

DESCRIPTION OF THE NEW VARIETY

Parentage: Seedling.
Parent: *Parthenocissus quinquefolia.*
Class: Vine.

The following is a detailed description of the new variety from specimens grown in Dayton, Oreg., in the month of July. The color terminology used is in accordance with The Royal Horticultural Society Colour Chart (R.H.S.C.C.) and refers to plate numbers in the afore-mentioned color chart. Phenotypic expression may vary depending on light, environmental and cultural conditions.

PLANT

A. Form: Vine-deciduous, clinging tendrils having about 5 to 8 branches each ending in adhesive tips.

B. Growth: Moderate, slower than species, typical branching.

*Height.*—20 to 35 feet, shape determined by supporting structure.

C. Foliage:

*Type.*—Compound palmate, 5 leaflets, each stalked.

*Size.*—Leaflet 1½ inches to 3 inches, generally smaller than species.

*Quantity.*—Single, alternate along stem, abundant.

*Color.*—Green with irregular patterns of white containing patches (splatters) of green. New foliage — Upper side: Larger areas of near 151D, splattered with near 154D. Underside: Same. Old foliage — Upper side: Large areas of near 135B, becoming near 56A in cool weather, and white to creamy white; white areas are splattered with near 189C, 191A and 191C, as well as near 135B. Underside: Similar to the grayed versions of upperside. Colder weather (Fall season): White areas become creamy yellow with rose pink coloration or tinge and green areas become near red.

*Shape.*—Elliptic to obovate-oblong.

*Texture.*—Upperside: Lustrous. Underside: Glaucescent.

*Veination.*—Regular branching.

*Edge.*—Serrate.

*Serration.*—Coarsely and often crenately serrate.

*Petiole.*—1 to 3 inches long Color stems and petiole: New stems near 141B; older stems light brown; petiole near 141B.

*Stipules.*—None-regular petiole.

*Auricle.*—Not present.

*Resistance to disease.*—Similar to species.

D. Wood:

*Old wood.*—Color: Light tan. Bark: Prominently lenticelled.

E. Winter hardiness: Winter hardy tested to at least USDA Zone 5 (−20° F.).

Reproductive Organs

A. Stamens, filaments and anthers: Numerous, irregularly arranged around style.

B. Styles: Short, thick.

C. Fruit:

*Shape.*—Globular berry.

*Size.*—About ¼ to ⅜" in diameter.

*Color.*—Bluish black.

I claim:

1. A new and distinct *Parthenocissus quinquefolia* plant variety substantially as shown and described.

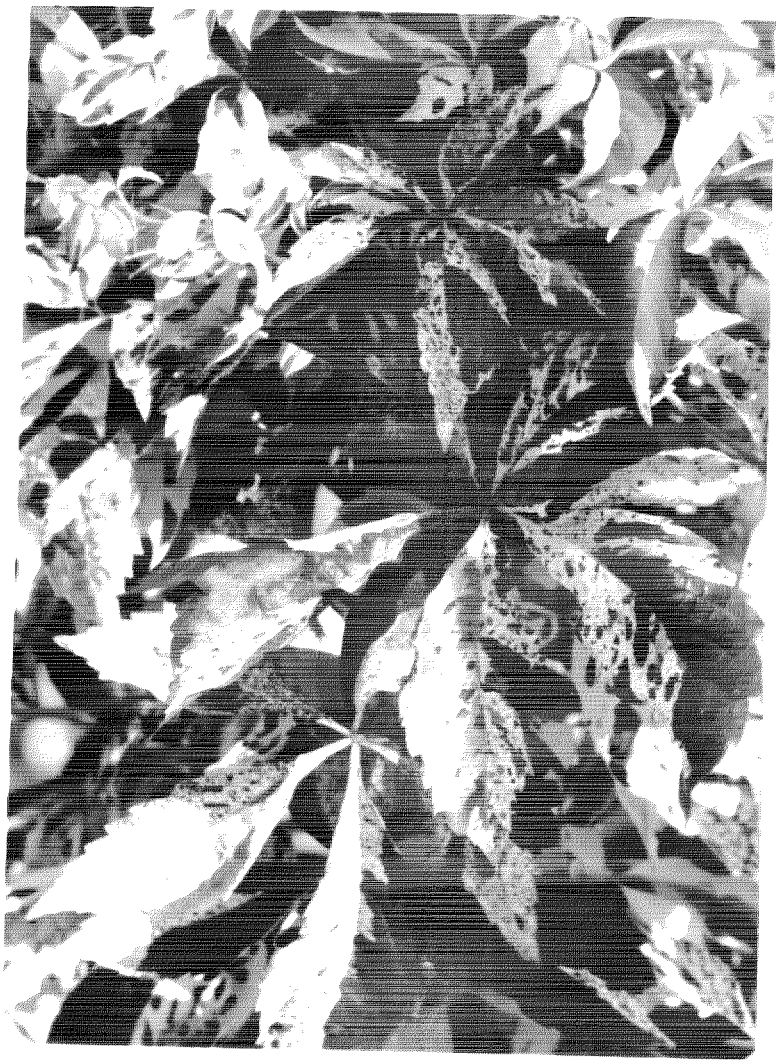

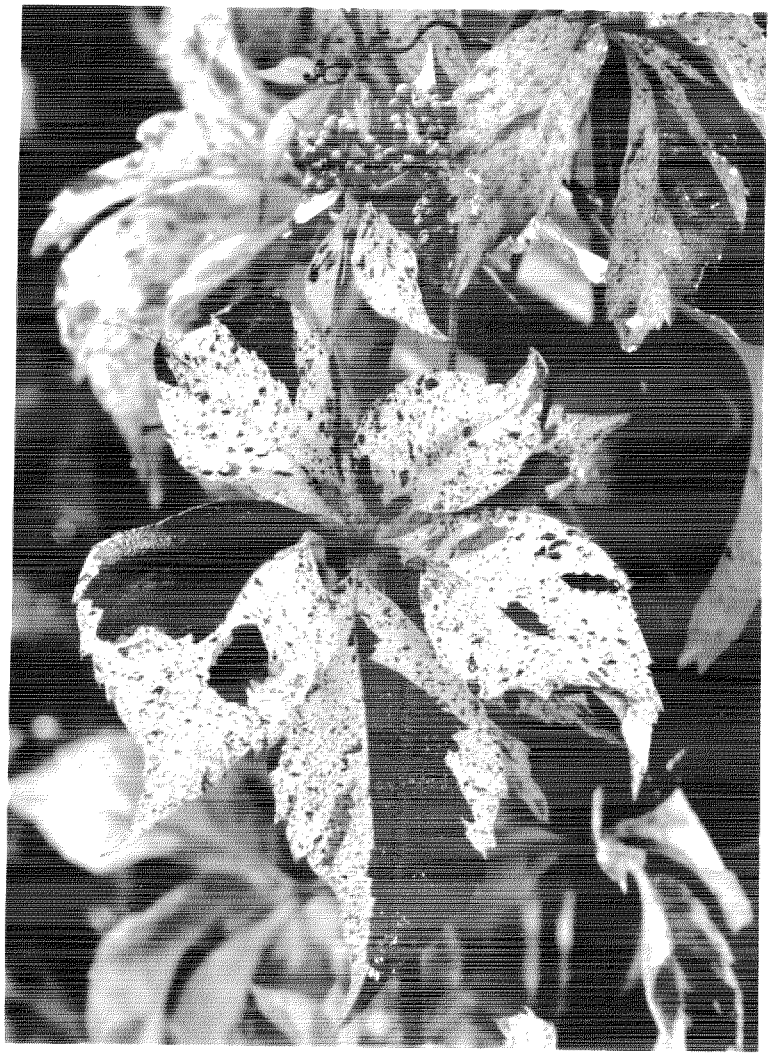

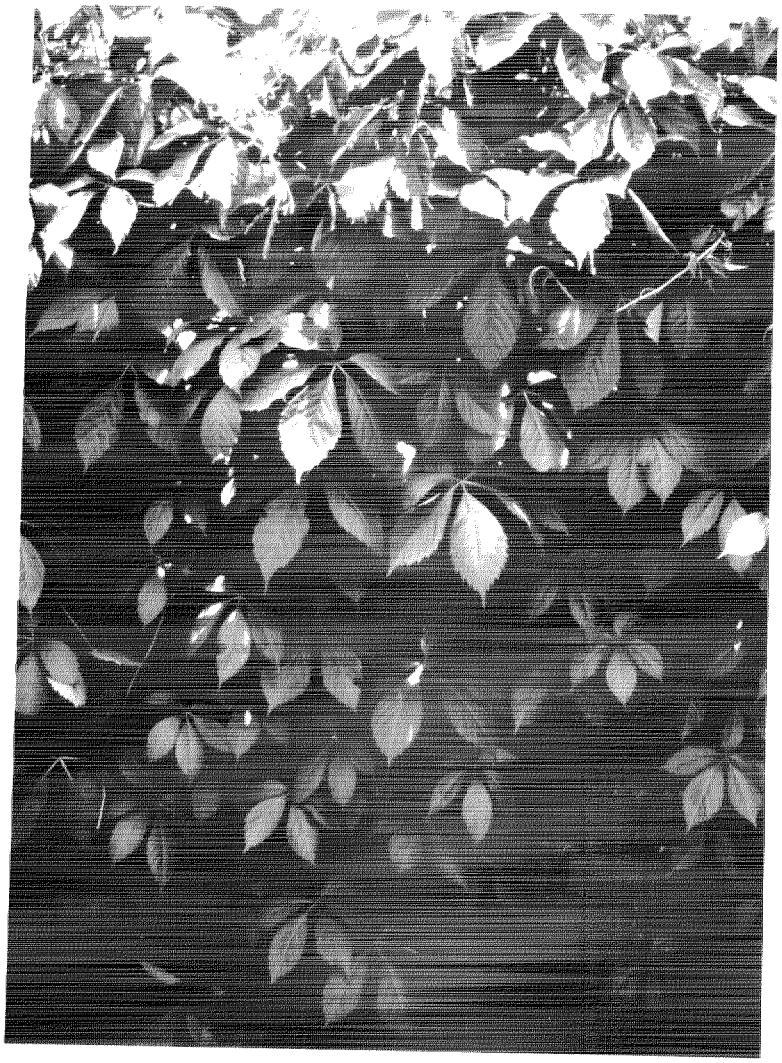

* * * * *